(12) United States Patent
Shikhman et al.

(10) Patent No.: US 10,485,962 B2
(45) Date of Patent: Nov. 26, 2019

(54) SYSTEM AND METHOD FOR DELIVERING THERAPEUTIC AGENTS TO THE UTERINE CAVITY

(71) Applicant: Menorrx, LLC, Trumbull, CT (US)

(72) Inventors: Oleg Shikhman, Trumbull, CT (US); Steven R. Goldstein, New York, NY (US)

(73) Assignee: Gynion, LLC, Trumbull, CT (US)

( * ) Notice: Subject to any disclaimer, the term of this patent is extended or adjusted under 35 U.S.C. 154(b) by 106 days.

(21) Appl. No.: 15/803,415

(22) Filed: Nov. 3, 2017

(65) Prior Publication Data

US 2018/0133446 A1 May 17, 2018

Related U.S. Application Data

(60) Provisional application No. 62/421,853, filed on Nov. 14, 2016.

(51) Int. Cl.
*A61M 31/00* (2006.01)
*A61B 18/06* (2006.01)
(Continued)

(52) U.S. Cl.
CPC .......... *A61M 31/002* (2013.01); *A61B 18/06* (2013.01); *A61B 2018/00559* (2013.01); *A61B 2018/00577* (2013.01); *A61M 5/484* (2013.01); *A61M 5/486* (2013.01); *A61M 25/1002* (2013.01); *A61M 2025/105* (2013.01); *A61M 2025/1075* (2013.01); *A61M 2205/15* (2013.01); *A61M 2209/01* (2013.01); *A61M 2210/1425* (2013.01); *A61M 2210/1433* (2013.01)

(58) Field of Classification Search
CPC .......... A61B 18/06; A61B 2018/00559; A61B 2018/00577; A61M 2025/105; A61M 2025/1075; A61M 2205/15; A61M 2209/01; A61M 2210/1425; A61M 2210/1433; A61M 25/1002; A61M 31/002; A61M 5/484; A61M 5/486
See application file for complete search history.

(56) References Cited

U.S. PATENT DOCUMENTS 3,645,265 A 2/1972 Majzlin
5,349,468 A 9/1994 Rathbone et al.
(Continued)

OTHER PUBLICATIONS

International Search Report and Written Opinion dated Sep. 2, 2013 in International Application No. PCT/US2013/045566.
(Continued)

*Primary Examiner* — Brandy S Lee
(74) *Attorney, Agent, or Firm* — Neil D. Gershon

(57) ABSTRACT

Apparatus for delivering a therapeutic agent to a uterine cavity including an elongated member having a fluid channel for passage of the therapeutic agent into the uterine cavity, a dispensing member extending distally of the elongated member and having at least one perforation for passage of the therapeutic agent into the uterine cavity into contact with the endometrium. An infusion line is in communication with the fluid channel for passage of a fluid into the uterine cavity to assess leakage to determine integrity of the uterine cavity prior to passage of the therapeutic agent into the uterine cavity.

13 Claims, 9 Drawing Sheets

(51) Int. Cl.
*A61M 5/48* (2006.01)
*A61M 25/10* (2013.01)
*A61B 18/00* (2006.01)

(56) References Cited

U.S. PATENT DOCUMENTS

| | | |
|---|---|---|
| 5,800,493 A | 9/1998 | Stevens et al. |
| 5,891,457 A | 4/1999 | Neuwirth |
| 6,066,132 A | 5/2000 | Chen et al. |
| 6,395,012 B1 | 5/2002 | Yoon et al. |
| 6,706,026 B1 | 3/2004 | Goldstein et al. |
| 7,063,670 B2 | 6/2006 | Sampson et al. |
| 8,343,078 B2 | 1/2013 | Toth |
| 9,498,597 B2 | 11/2016 | Goldstein et al. |
| 9,907,601 B2 | 3/2018 | Cressman |
| 9,983,907 B2 | 5/2018 | Li et al. |
| 2003/0049302 A1 | 3/2003 | Pauletti |
| 2005/0288660 A1 | 12/2005 | Ryan et al. |
| 2007/0066990 A1 | 3/2007 | Marsella et al. |
| 2008/0058797 A1 | 3/2008 | Rioux |
| 2009/0048609 A1 | 2/2009 | Atiomo |
| 2009/0069883 A1* | 3/2009 | Ding .................. A61F 2/86 623/1.42 |
| 2009/0138000 A1 | 5/2009 | Vancelette et al. |
| 2009/0306588 A1 | 10/2009 | Nguyen et al. |
| 2009/0287300 A1* | 11/2009 | Dave .................. A61L 31/06 623/1.42 |
| 2010/0087798 A1 | 4/2010 | Adams |
| 2010/0121319 A1* | 5/2010 | Chu .................... A61B 18/18 606/33 |
| 2013/0090572 A1* | 4/2013 | Peliks ................. A61B 5/4325 600/591 |
| 2015/0141963 A1* | 5/2015 | Goldstein ........... A61B 17/42 604/515 |
| 2015/0335373 A1 | 11/2015 | Chee et al. |
| 2018/0133446 A1 | 5/2018 | Shikhman et al. |

OTHER PUBLICATIONS

Extended European Search Report dated Jul. 2, 2017 in European Patent Application No. 13803886.4.
International Search Report and Written Opinion dated Nov. 5, 2018 for International Application No. PCT/US2017/059995.

* cited by examiner

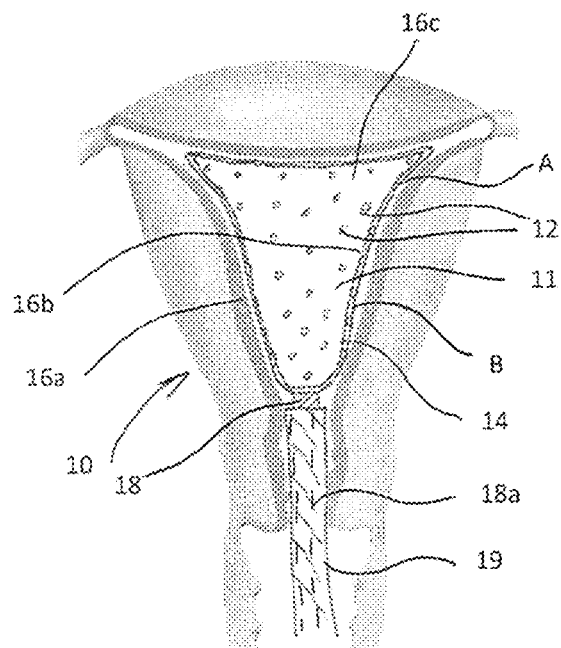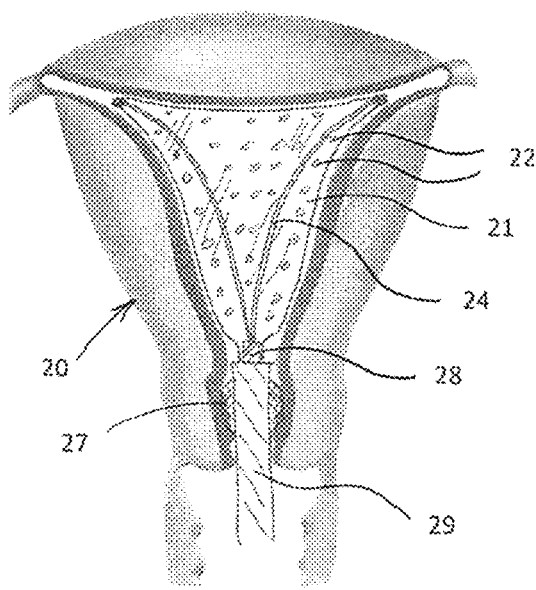
Fig. 1　　　Fig. 2
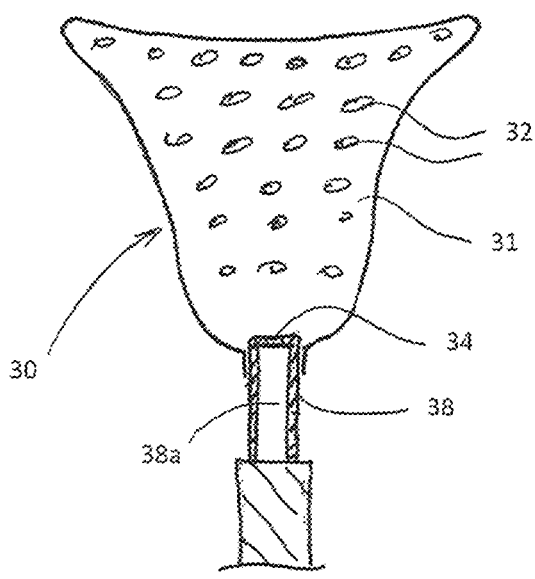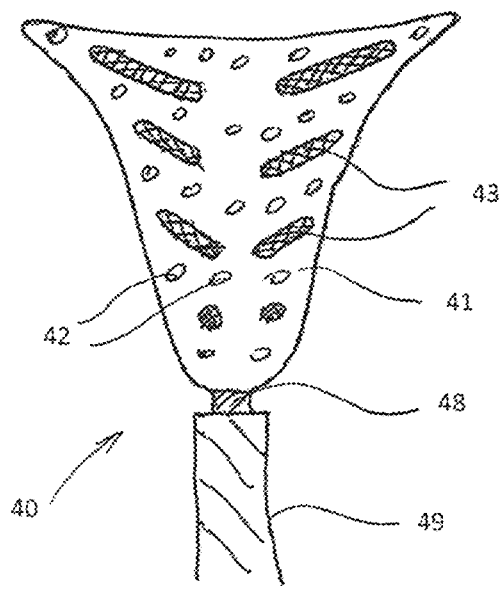
Fig. 3　　　Fig. 4

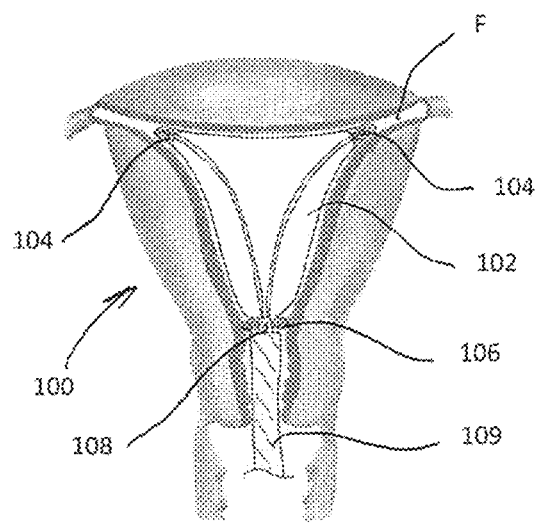
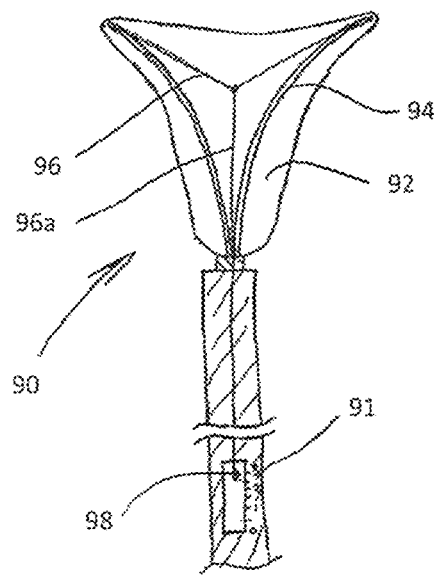
Fig. 11
Fig. 12
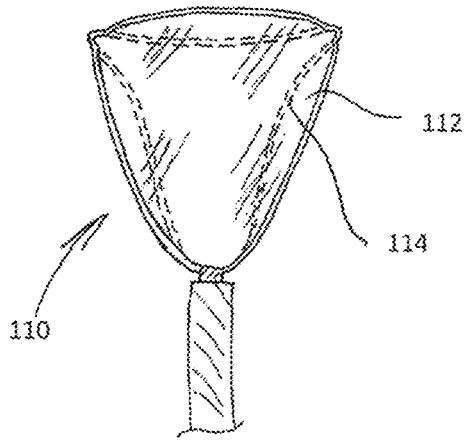
Fig. 13

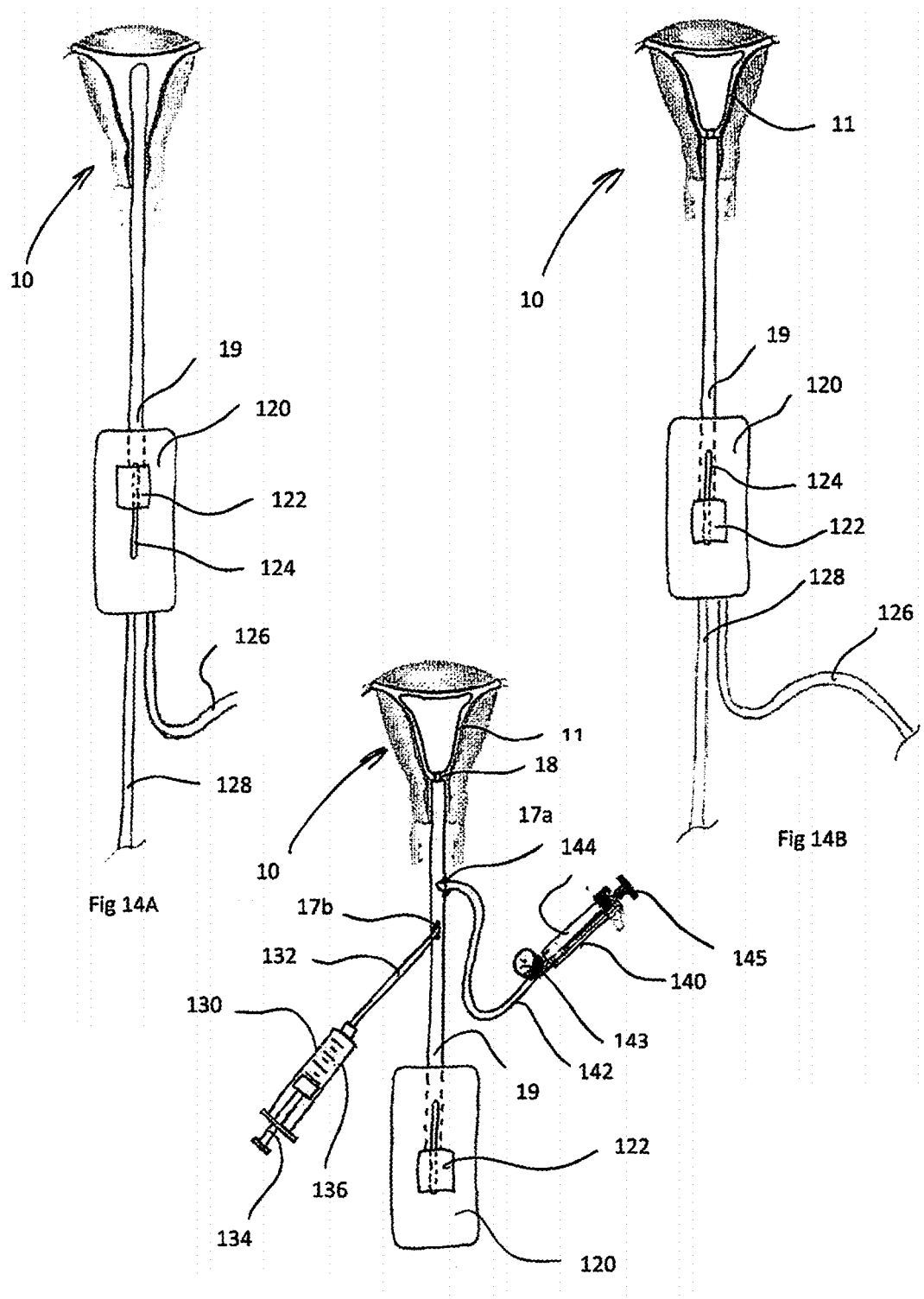

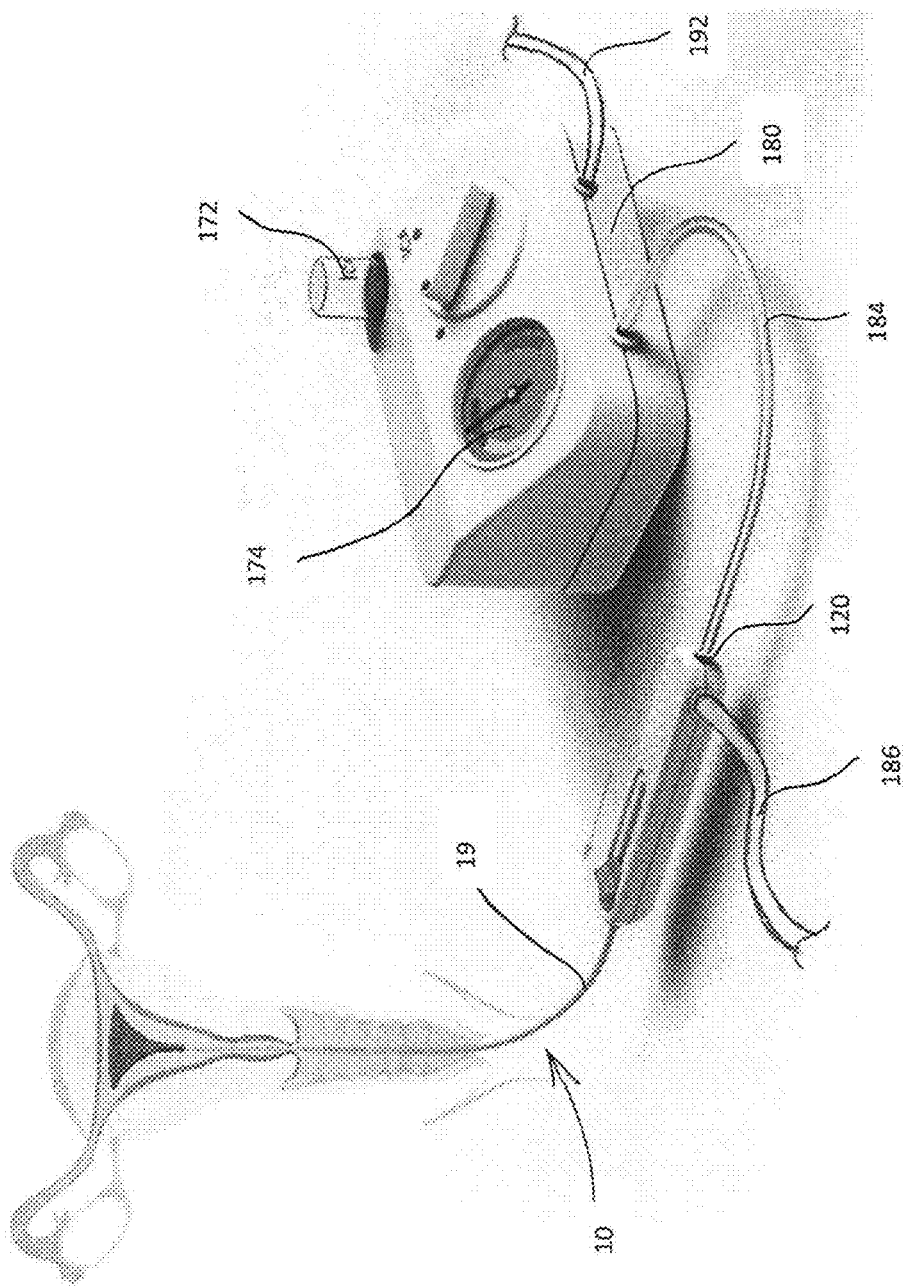

SYSTEM AND METHOD FOR DELIVERING THERAPEUTIC AGENTS TO THE UTERINE CAVITY

This application claims priority from provisional application Ser. No. 62/421,853, filed Nov. 14, 2016, the entire contents of which are incorporated herein by reference.

BACKGROUND OF THE INVENTION

1. Field of the Invention

This application relates to a system and method for delivering therapeutic agents to a patient and, more specifically, to a uterine cavity for endometrial ablation.

2. Background

Abdominal Uterine Bleeding (AUB) is excessive bleeding from the vagina that lasts more than seven days. Heavy periods can cause pain and discomfort and increase the risk of iron-deficiency anemia. Acute excessive bleeding can lead to hemodynamic instability, requiring hospitalization for fluid volume management, blood transfusion, and/or intravenous estrogen. This condition has a significant negative impact on woman's sexual functioning, mental well-being and overall health.

Studies have shown that Abdominal Uterine Bleeding affects approximately 1 in 3 women in their lifetime. This is over 200 million women worldwide. In the U.S. alone, there are ten million women suffering from AUB with 200,000 newly diagnosed women each year. The conservatively estimated annual direct economic cost of AUB in the US is approximately $1-1.55 billion and indirect cost is $12-36 billion.

There are four groups of treatment options that are currently available for treating AUB: 1) Dilatation and Curettage (D&G); 2) Hysterectomy; 3) Intrauterine device (IUD) and 4) Global endometrial ablation (GEA). Each of these treatments has significant disadvantages. Dilation and Curettage offers a short-term relief and has a high risk of perforations. This option is not in wide use. Hysterectomy is a surgical removal of the uterus, which involves major surgery done under general or regional anesthesia. Due to its invasive nature, high costs and risks, the number of these procedures has dropped over 50% in the last decade. Intrauterine devices, such as the Bayer HealthCare' "Mirena" IUD, are not highly effective and have significant side effects and risks. Use of the Mirena IUD to control heavy menstrual bleeding in women seeking contraception has increased in popularity. This is mainly because many clinicians are uncomfortable with the existing methodologies which require extensive training and skill as well as anesthesia and are mostly performed in "OR setting" facilities. However, due to ease-of-use and relatively low cost of this treatment option, the use has been growing. Global Endometrial Ablation devices, such as the Hologic "NovaSure", the Boston Scientific "Genesys HTA" and the Cooper Surgical "Her Option", are currently being utilized to ablate endometrium. The procedure can be done in a hospital setting or in the office. This is the most common option for treatment of AUB in the U.S. The procedure has demonstrated high efficacy, but is rather complex for in-office use and relatively expensive. Thus, GEA and IUD devices are the primary options for AUB treatment that are currently offered.

Endometrial ablation techniques, which have evolved as an alternative to hysterectomy, (e.g., laser, resecting loop with electric current, electric rollerball, thermal fluid-filled balloon, radiofrequency, freezing, heated saline) remove some of the lining of the uterus in an attempt to control excessive bleeding. After endometrial ablation, pregnancy is not likely to occur.

The early techniques of endometrial ablation, introduced in the 1980s and still used today (although much less commonly) involve the use of a hysteroscope with either a "rollerball" or wire loop through which electrical heat travels to remove (resection) the endometrial lining. After the uterus is filled with fluid to enlarge it for better viewing, the surgeon moves the rollerball back and forth across the lining or uses the wire loop to shave off the tissue. Potential risks of this ablation method include infection, perforation of the uterus, cervical laceration, and fluid overload.

In 1997, the Food and Drug Administration (FDA) approved ThermaChoice, the first non-hysteroscopic ablation device to treat excessive uterine bleeding (menorrhagia) due to benign (non-cancerous) causes. The Gynecare ThermaChoice Uterine Balloon Therapy System has a balloon that is inserted through the neck of the cervix and into the uterus. Through a catheter connected to a controller console, the balloon is inflated with fluid and heated to 188° F. (87° C.) for 8 minutes to destroy the uterine lining.

In 2001, the FDA approved three more similar devices. These devices are to be used only in women who have not yet reached menopause and whose child-bearing is completed. The BEI Medical Systems Hydro ThermAblator delivers heated saline solution into the uterus. The heated saline solution is delivered using hysteroscopic guidance. The heated solution destroys the uterine lining in about ten minutes. The CryoGen Her Option Uterine Cryoblation Therapy System uses a cryoprobe capable of producing temperatures down to minus 148° F. (minus 100° C.) at the tip. This extreme cold is applied to the tissue for ten minutes to freeze and destroy the uterine lining. Ultrasound is used to guide and monitor the procedure.

Currently available AUB treatment options are either invasive, ineffective, expensive or have a combination of these limitations. As a result, the market penetration for existing pharmaceutical and therapeutic options remains very low. Studies show that only 15.8% of patients received a therapeutic procedure within twelve months, post diagnosis. Studies also show that 38% of women with AUB undergo a hysterectomy, which is a major surgery, without even being offered less invasive alternatives. These studies show that physicians and patients are well-aware of these limitations and reluctant to use these treatment options.

There is a need for a non-invasive, easy-to-use (short learning curve), and effective device for treating AUB. It would further be advantageous to provide such treatment with a low cost device and low procedural costs. This would enable treatment of the patient population that currently remains untreated due to clinical and economic limitations of the current options. It would also be advantageous if such device ensured that the therapeutic agent is safely delivered to the endometrium in the uterine cavity.

SUMMARY

The present invention overcomes the deficiencies and disadvantages of the prior art. The present invention advantageously provides in preferred embodiments an apparatus for endometrial ablation that is easy to use, economical and controls the pressure of therapeutic agent applied to the endometrium. The apparatus of the present invention also in preferred embodiments apply a pre-check of the uterine cavity to ensure it is sealed before application of the therapeutic agent, thereby preventing exposure to other areas of the body. The therapeutic agent is preferably injected at a controlled pressure to maximize the surface of exposure of the endometrium (preferably the entire surface will be exposed) to the agent while preventing leakage to other areas.

In accordance with one aspect of the present invention, an apparatus for delivering a therapeutic agent to the uterine cavity of the patient is provided having an elongated member having a fluid channel for passage of the agent into a uterine cavity of a patient. The fluid channel has an opening. The dispensing member extends distally of the elongated member and is in communication with the fluid channel and has at least one perforation to provide exit openings for passage of the agent into the uterine cavity into contact with the endometrium, the agent injectable through the at least one perforation at a controlled pressure. In preferred embodiments, the therapeutic agent is a chemical agent for endometrial ablation.

In some embodiments, the dispensing member has a first condition for delivery having a first transverse dimension and a second condition for placement within the uterine cavity having a second transverse dimension greater than the first transverse dimension.

In accordance with another aspect of the present invention, an apparatus for delivering a therapeutic agent to the uterine cavity of the patient is provided having an elongated member having a fluid channel for passage of the therapeutic agent into the uterine cavity. The fluid channel has an opening. A dispensing member extends distally of the elongated member and has at least one perforation to provide for passage of the therapeutic agent into the uterine cavity into contact with the endometrium. An infusion line is in fluid communication with the fluid channel for passage of a fluid into the uterine cavity to assess leakage to determine integrity of the uterine cavity prior to passage of the therapeutic agent into the uterine cavity and the agent is injected at a controlled pressure. In preferred embodiments, the therapeutic agent is a chemical agent for endometrial ablation.

In some embodiments, the dispensing member has a first transverse dimension in a first condition for delivery to the uterine cavity and a second transverse dimension in a second condition for placement within the uterine cavity, the second transverse dimension being greater than the first transverse dimension.

In accordance with another aspect of the present invention, a system for delivering a therapeutic agent to the uterine cavity of the patient is provided having an elongated member having a fluid channel for passage of the agent into contact with the endometrium and a dispensing member extending distally of the elongated member. The dispensing member has a plurality of perforations to provide exit openings for passage of the agent into the uterine cavity into contact with the endometrium. A console has a pressure gauge, a receptacle to receive the agent, and a switch to control injection of the agent through the fluid channel of the elongated member. In some embodiments, the console includes a port to receive a tube from a source of pressurized fluid, the pressurized fluid injectable through the fluid channel into the uterine cavity to assess the presence or absence of leakage in the uterine cavity, and the pressurized fluid is injectable in a first position of the switch. In some embodiments, the pressurized fluid is injectable into the agent in the receptacle to inject the agent through the fluid channel at a higher pressure and a controlled pressure, the pressurized fluid injectable into the agent in a second position of the switch.

In some embodiments, dispensing member has a first condition for delivery having a first transverse dimension and a second condition for placement within a uterine cavity having a second transverse dimension greater than the first transverse dimension.

In accordance with another aspect of the present invention, a console for controlling fluid flow to a uterine cavity for an endometrial ablation procedure is provided, the console comprising a pressure gauge, a receptacle to store a chemical ablative agent, and a switch to control fluid flow. The switch has a first position to prevent fluid flow, a second position to enable pressurized fluid to flow into the uterine cavity and a third position to enable the pressurized fluid to flow into the receptacle to pressurize the ablative agent. In some embodiments, in the second position, the pressurized fluid flows into the uterine cavity to assess the presence of absence of leakage from the uterine cavity to check integrity of the uterine cavity.

In accordance with another aspect of the present invention, a method for injecting a therapeutic agent into the uterine cavity of the patient is provided comprising the steps of a) checking the integrity of a uterine cavity to determine if there is leakage from the uterine cavity; and b) if the integrity of the uterine cavity is confirmed, subsequently injecting the therapeutic agent into the uterine cavity under controlled pressure. In some embodiments, the integrity of the uterine cavity is checked by injection of pressurized fluid and a) determining if the pressure remains constant after injection of the pressurized fluid is terminated and/or b) determining if flow of the pressurized fluid ceases prior to being turned off. In some embodiments, the pressurized fluid is used to inject the therapeutic agent. In some embodiments, the therapeutic agent is a chemical ablation agent.

In some embodiments, the method further includes the step of moving a switch from a neutral position to a first position to align a first fluid line for injection of pressurized fluid. In some embodiments, the method further includes the step of moving the switch to a second position to align a second fluid line for injection of the pressurized fluid into the therapeutic agent to inject the agent at an increased pressure.

BRIEF DESCRIPTION OF THE DRAWINGS

So that those having ordinary skill in the art to which the subject invention appertains will more readily understand how to make and use the apparatus disclosed herein, preferred embodiments thereof will be described in detail hereinbelow with reference to the drawings, wherein:

FIG. 1 is a cross-sectional view of a first embodiment of the endometrial ablation apparatus of the present invention;

FIG. 2 is a cross-sectional view of an alternate embodiment of the apparatus of the present invention;

FIG. 3 is a cross-sectional view of another alternate embodiment of the apparatus of the present invention having a pressure reduction feature;

FIG. 4 is a cross-sectional view of another alternate embodiment of the apparatus of the present invention having a balloon reinforcement feature;

FIG. 11 is a cross-sectional view of another alternate embodiment of the apparatus of the present invention having a plurality of plugs to seal the uterine cavity;

FIG. 12 is a cross-sectional view of another alternate embodiment of the apparatus of the present invention having a balloon width indicator;

FIG. 13 is a cross-sectional view of another alternate embodiment of the apparatus of the present invention having an enlarged balloon;

FIG. 14A is a plan view illustrating the apparatus of FIG. 2 with an output suction tube and a fluid input tube, and further showing the actuator in the first position wherein the dispensing member is confined within the outer tube and FIG. 14B is a view similar to FIG. 14A with the actuator in the second position to expose the dispensing member to allow expansion within the uterine cavity;

FIG. 15 is a plan view of an alternative system of the present invention having a syringe for injecting fluid to check the integrity of the uterine cavity and a syringe to inject an ablative agent;

FIG. 16 is a perspective view of an alternative embodiment of the present invention system showing delivery catheter and the console containing the selector switch for controlling fluid flow;

DETAILED DESCRIPTION OF PREFERRED EMBODIMENTS

Figure 5:
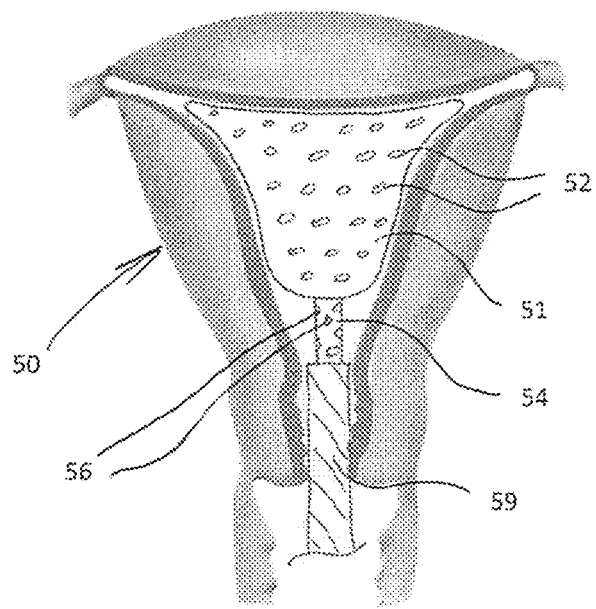
FIG. 5 is a cross-sectional view of another alternate embodiment of the apparatus of the present invention having apertures in the shaft for dispensing the therapeutic agent.

The present invention provides a chemical global endometrium ablation apparatus (device) for the treatment of Abnormal Uterine Bleeding (AUB). The apparatus advantageously performs one or more multiple functions including: 1) providing a cavity integrity checking feature to ensure absence of perforations, that the fallopian tubes are closed and the uterine cavity sealed prior to injection of the chemical agent; 2) expanding a dispensing member inside the uterine cavity adjacent the endometrium (the membrane that lines the inside of the uterus wall); and/or 3) injecting at sufficient pressure the chemical agent at a desired controlled pressure through the dispensing member for application of the agent to the endometrium. The therapeutic agent is preferably injected at a controlled pressure to maximize the surface of exposure of the endometrium (preferably the entire surface will be exposed) to the agent while preventing leakage to other areas. In the absence of perforations, and when a cervical canal is sealed by the device, the uterine cavity should be sealed as long as injection pressure will remain below the pressure that is necessary to open fallopian tubes that are naturally collapsed. Therefore, there are two pressure limits: 1) the upper to prevent leakage and 2) the lower to assure maximum exposure.

The apparatus can also include a sealing member to seal the cavity from leaks of the chemical agent or air through the cervix and/or into the fallopian tubes. In some embodiments of the present invention, the apparatus includes a switch which is maneuverable by the clinician to achieve the foregoing functions in the single device, as discussed in more detail below.

The present invention in alternative embodiments also includes systems that instead of a manifold include separate devices. e.g., syringes, connectable to the apparatus downstream of the handle to inject fluid and gas through the fluid channel in the apparatus for agent delivery and cavity integrity checking. These embodiments are also discussed in detail below.

The apparatus is designed in preferred embodiments to deliver the therapeutic agent in the form of a liquid chemical agent (substance) for a chemical endometrial ablation procedure. One cauterizing agent which can be used is an acid such as trichloroacetic acid (TCA). Derivatives of trichloroacetic such as bichloroacetic acid, and other substances such as silver nitrate, and derivatives of silver nitrate can also be utilized in certain embodiments. TCA is a chemical agent that denatures on contact with protein and causes chemical cauterization on contact with tissue, but does not spread beyond where it is directly applied. Additionally, instead of chemical agents, other therapeutic agents can be delivered, the devices/systems herein not being limited to chemical endometrial ablation as for example a specially formulated substance, such as a therapeutic agent in the form of a drug with a pharmaceutical formula that is specially formulated for this application can be utilized.

Additionally, although disclosed for use within the uterine cavity for endometrial ablation, the apparatus and systems disclosed herein are not so limited and can be used for treatment of other conditions and/or for treatment in other areas (cavities) of the body.

As used herein, the term 'proximal' denotes the portion of the device closer to the user and the term "distal" denotes the portion of the device further from the user. Also, the terms apparatus and device are used herein interchangeably.

Turning now to the dispensing member (element/component) of the apparatus of the present invention, various embodiments are shown in FIGS. 1-13. The dispensing member forms the agent dispensing or dispersing member for enabling passage of the injected agent into the uterine cavity into contact with the endometrium. The dispensing member in these embodiments is expandable and configured to maximize the area of endometrial tissue that is exposed to the agent injected through the perforations in the member. In some embodiments, the dispensing element expands to a size so it is adjacent but not in contact with the endometrium to provide space for flow of the agent from the dispensing member to the endometrium. In alternate embodiments, the dispensing member can be configured to expand to the contour of the uterus and into contact with the endometrium to fully fill the uterine cavity. In other embodiments, the dispensing member is not expandable. Note FIGS. 1-13 show the distal end of the apparatus which has the expandable dispensing member it being understood that the proximal end, e.g., handle is omitted from these drawings. The expandable dispensing member can be in the form of a perforated (pierced) balloon, a pad made out of porous material, a porous material such as foam or a sponge-like material, a foam inside a balloon, or in the form of a series of apertured tubes. The therapeutic agent can then flow though the perforations or pores in the expanded dispensing member and into contact with the endometrium. For delivery, the dispensing member is in a collapsed or low profile (smaller transverse dimension) condition and expands to a larger transverse dimension within the uterine cavity.

Referring now in detail to the drawings wherein like reference numerals identify similar or like components throughout the several views, a first embodiment of the expandable member is shown in FIG. 1. The apparatus 10 includes a balloon 11 having a plurality of perforations 12 extending through the wall to enable communication of fluid from the interior of the balloon to the uterus B, i.e., endometrium A. The perforations 12 are shown dispersed throughout the wall of the balloon to provide sufficient application of therapeutic agent, e.g., chemical agent, to the endometrium. The perforations can in some embodiments be uniformly positioned to provide uniform application of agent so the agent is spread evenly through the endometrial cavity for uniform adequate ablation. In some embodiments, a pre-calculated volume of agent at a controlled pressure is injected into the balloon. In other embodiments, the agent is injected without volume calculation until a target controlled pressure within the uterine cavity is achieved.

Note that as an alternative to the balloon 11, as well as an alternative to the other embodiments of balloons disclosed herein, a foam material, sponge, or other material that expands and has perforations or pores to enable application of the agent to the lining of the uterus (endometrium) can be utilized. Additionally, the balloon can be filled with a foam. In any of these embodiments, the size of the holes of the balloon (or foam material, sponge, etc.) can be varied to control the flow and volume of the agent in different areas of the balloon.

Balloon 11 may also include a support wire 14 which expands the balloon 11, i.e., forces the balloon 11 open. The wire 14 facilitates expansion to maximize the exposure area of the balloon with respect to the endometrium. The wire 14 can be made of material with sufficient springiness or of shape memory material so that when deployed from the outer tube or sheath 19, it moves from its collapsed or compressed condition inside sheath 19 to an expanded position of larger transverse dimension shown in FIG. 1. Note the wire 14 is shown positioned along the entire periphery of the balloon to expand the balloon 11.

The balloon 11 and supporting/expanding wire 14 are supported, e.g., attached, at a distal end on shaft 18 which is movable relative to sheath 19. That is, for delivery to the uterus, the wire 14 and balloon 11 are retained inside the sheath 19 as the shaft 18 is retracted within the sheath 19. To deploy the balloon 11 and wire 14, the sheath 19 is retracted, the shaft 18 is advanced distally or both the sheath 19 and shaft 18 are moved relative to one another so that the balloon 11 and wire 14 are distal of the sheath 19 and exposed from the confines of the sheath wall, the term "relative movement" or "movement relative to" encompassing these three alternatives. Exposure of the balloon 11 and wire 14 from the confines of sheath 19 enables expansion of the balloon 11 due to expansion of the wire 14. The agent is injected through channel or lumen 18a in shaft 18, the channel 18a having a distal opening in communication with the interior of balloon 11 so the agent (e.g., chemical ablative substance/agent) flows through the channel, exiting the distal opening into the interior of balloon 11. In addition to the channel for delivery of the agent to the dispensing member, additional channels could be provided for use for other purposes, such as a separate channel for inflation of the balloon, insertion of other instruments, tools, scope, camera, etc.

Markings can be provided on sheath 19 to indicate the depth of insertion of the apparatus 10 into the uterine cavity. Markings can also be provided on shaft 18 to indicate the extent of exposure from the sheath 19. The outer sheath 19 is configured for ease of insertion through the cervix and in some embodiments is sized such that it would require no or minimum dilation of the cervix prior to insertion.

The structural wire 14 as shown in FIG. 1 extends along the periphery of the balloon 11, with portions 16a, 16b extending distally from the distal end of shaft 18 and a portion 16c extending transversely to portions 16a, 16b. A single wire shaped as shown or separate wires attached in the illustrated configuration can be utilized. In alternate embodiments, the wire 14 can have other configurations/shapes and/or be positioned in other regions of the balloon such as shown for example in the embodiment of FIG. 2. In this embodiment of FIG. 2, wire 24 of device 20 is positioned more inwardly of the periphery of balloon 21. The balloon 21 of FIG. 2 is otherwise identical to balloon 11 of FIG. 1, e.g., has perforations 22, is supported on shaft 28 which is slidable with respect to sheath 29, etc., so for brevity further description is not provided as the function and structure of the elements of FIG. 1, e.g., shaft, sheath, balloon, etc., are fully applicable to the embodiment of FIG. 2. Note that the wire is shaped to facilitate full deployment of the balloon (dispensing member) 21. That is, wires 14 and 24 are utilized to assure that the dispensing member is expanded to maximize the exposure area as the wire reinforces the balloon and is used to force the balloon to open up. The size of the holes in the pierced balloon could vary to control the flow and the volume of the substance in different areas of the balloon. A sealing member such as a balloon or plug 27 is provided around the sheath (FIG. 2) to seal the cervical canal to prevent outflow of fluid, e.g., $CO_2$ or $H_2O$ and the therapeutic agent.

In some embodiments utilizing a structural wire to expand the balloon, the balloon expansion is independent of the therapeutic agent. In this manner, the agent dosage can be determined solely by the clinical need to effectively perform ablation or other treatment rather than requiring sufficient injection to first inflate the balloon, followed by passage through the balloon. In other words, in such embodiments, the agent is not used for balloon inflation but only for dispensing through the balloon, independent of the expansion by the internal wire. By relying on mechanical expansion, it also enables agent pressure to be minimized so excessive pressure is not applied. The balloons can be made for example of a non-compliant elastomeric material such as polyethylene, although other materials are also contemplated.

It is also contemplated that in alternate embodiments, instead of a wire to expand the balloon in the various embodiments disclosed herein, the balloon can be expanded by the pressure of the injection fluid.

In the alternate embodiment of FIG. 3, the balloon 31 (dispersing/dispensing member) of apparatus 30 is similar to balloon 11 in that it has a plurality of perforations 32 for dispensing the chemical agent. The apparatus 30 differs from device 10 in that the shaft 38 movable relative to shaft 30 has a "pressure reduction" feature designated by reference numeral 34. The pressure reduction feature 33 is shown in the form of an aperture 34 at the end of the channel (lumen) 38a within shaft 38 having a diameter less than the diameter of the shaft 38 so that pressure within the balloon 31 is lower than pressure within the delivery channel. This provides injection of the agent at a lower pressure.

The balloons disclosed herein can include welded areas, such as areas 43 of balloon (dispensing member) 41 of device 40 shown in FIG. 4. These strips provide additional rigidity to the balloon walls so that the opposite walls of the balloon are substantially parallel to each other to maximize surface contact with anterior and posterior walls of the uterine cavity. That is, they keep the balloon expanded in essentially two dimensions, e.g., substantially flat. Balloon 41 has perforations 42 and is supported on shaft 48, movable relative to the sheath 49, in the same manner as shaft 18 described above. Balloon 41 can include the internal expandable wire structures, e.g., wires 14 or 24, disclosed herein.

In the embodiments disclosed herein, the shaft (elongated member0 could have additional perforations to maximize exposure in cases where the length of the cavity exceeds the length of the dispensing member. This is shown for example in FIG. 5 wherein apparatus 50 has a dispensing member 51 in the form of a balloon with perforations 52 like perforations 22 described above. An internal reinforcing expanding wire structure, like wire 14 or 24 described herein, can be provided within the balloon 51. Shaft 54 has a channel or lumen extending therein with an opening in communication with the interior of balloon 51 for passage of injected agent into the interior of balloon 51 for exiting perforations 52. Shaft 54 further has a plurality of perforations 56 in its side wall, proximal of the balloon 52, to provide additional flow of agent into the uterine cavity and endometrium. It would also potentially allow exposure of tissue within the cervical canal. The shaft 54 is relatively slidable with respect to sheath (outer tube) 59 in the same manner as aforedescribed shaft 18 and sheath 19.

Figure 6:
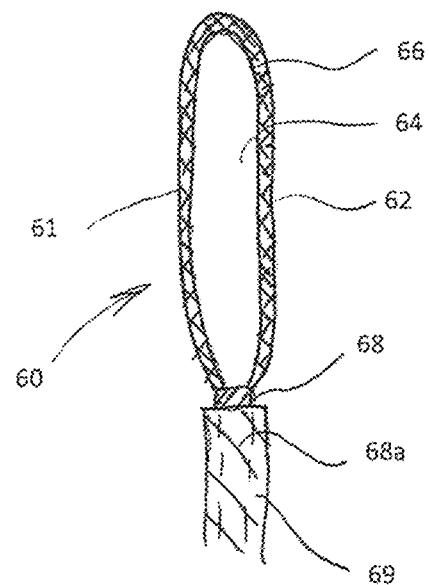
FIG. 6 is a cross-sectional view of another alternate embodiment of the apparatus of the present invention having a double walled balloon to form a space for the therapeutic agent within the wall.
Figure 7A:
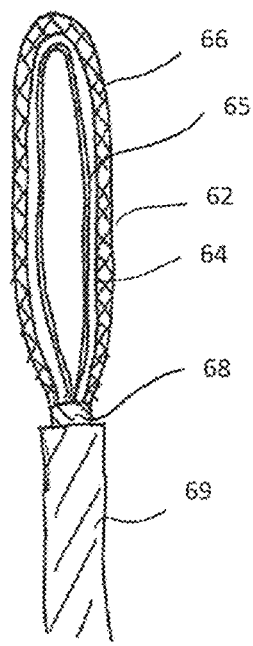
FIG. 7A is a cross-sectional view of the double walled balloon showing the internal wire and FIG. 7B illustrates one method to form the double balloon of FIG. 6.
Figure 7B:
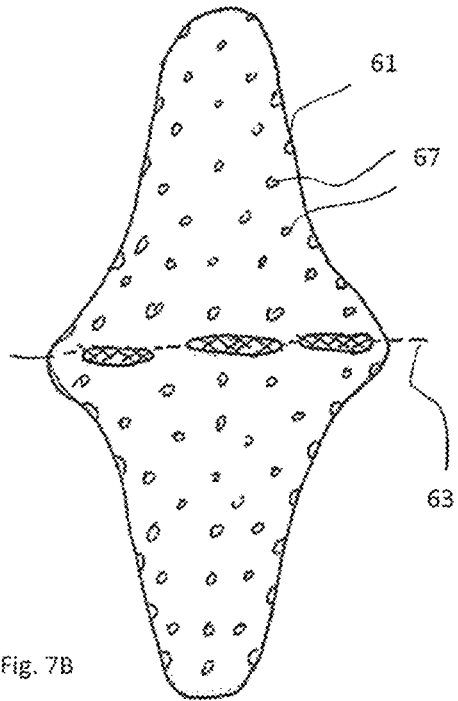

FIGS. 6, 7A and 7B show an alternate embodiment of a dispensing member in the form of a double walled balloon (or a balloon within a balloon) wherein the therapeutic agent is injected into the space between the wall of the balloon or the wall between the outer and inner balloon. More specifically, balloon 61 of apparatus 60 has an outer wall 62 and an inner wall 64, spaced apart sufficiently to create sufficient space/volume for the agent. The channel 68a of shaft 68 is in fluid communication with the space (balloon channel) 66 between balloon walls 62 and 64 so the agent can flow through the channel, into the space 66 and out through perforations 67 in outer wall 62. The inner space of the balloon can be filled with a fluid, i.e., a gas, e.g., air or liquid and/or an expanding internal wire 65 (see FIG. 7A) similar to wires 14 or 24 to aid expansion. (Fluid as defined herein including a gas or liquid). By injecting the agent only into the reduced space/volume provided between the inner and outer wall, rather than though the internal space/volume of the balloon, the injectable volume of the agent is minimized thereby minimizing unnecessary patient exposure to excessive amount of agent.

One possible way to form the balloon 61 is shown in FIGS. 7A and 7B wherein the balloon 61 has a fold line 63. The balloon is initially in a more flattened condition (FIG. 7B) and then folded along fold line 63 and then sealed along its periphery to join the walls of the balloon 61 to create the inner and outer spaced apart walls. The shaft 68 and sheath (outer tube) 69 are relatively slidable in the same manner as aforedescribed shaft 18 and sheath 19.

Figure 10A:
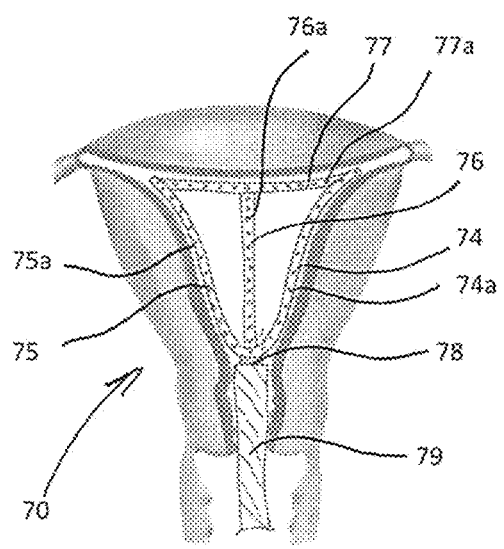
FIGS. 10A-10D are cross-sectional views of alternate embodiments of the apparatus of the present invention having a plurality of perforated tubes.
Figure 10B:
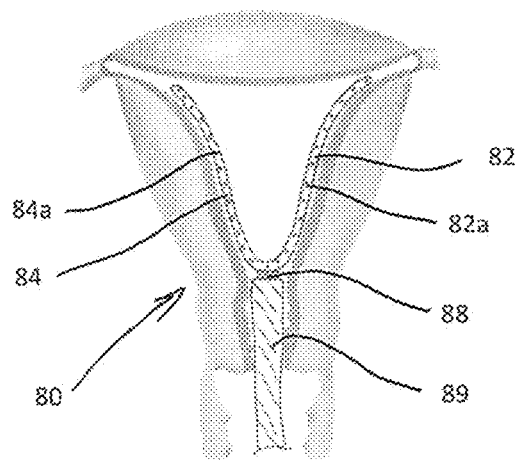
Figure 10C:
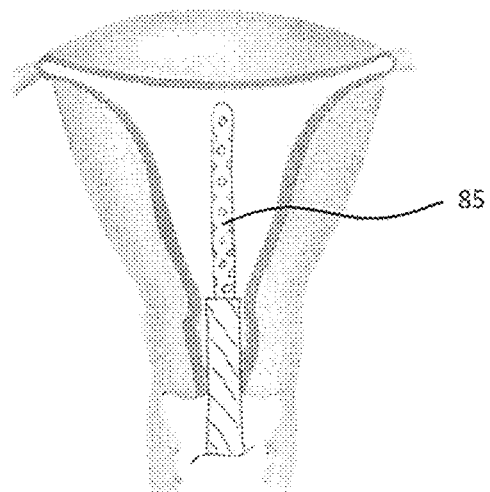
Figure 10D:
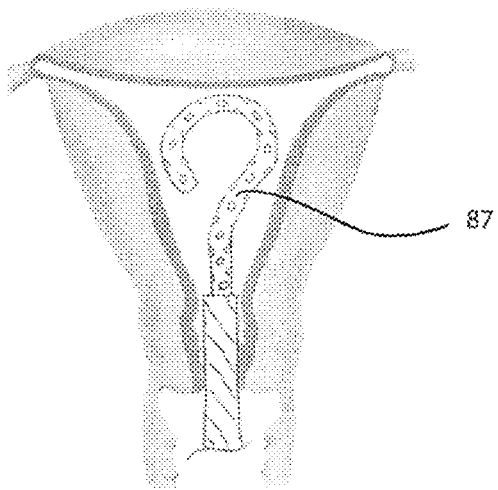

As mentioned above, as an alternative to a balloon, sponge, foam or other porous or perforated material, the dispersing/dispensing member can include one or more perforated tubes In FIG. 10A, apparatus 70 has an elongated member (shaft) 78 coaxially positioned within outer tube or sheath 79, and slidable relative to sheath 79. Extending from shaft 78 are a network (series) of tubes including two distally directed curved side tubes 74, 75, a longitudinally extending tube 76 and a transverse tube 77, forming a closed shaped configuration as shown. The tubes 74, 75, 76 and 77 each have perforations 74a, 75a, 76a and 77a, respectively, through which the therapeutic agent exits. The agent flows through a channel in the shaft 78 and into the channel or lumen within the tubes 74-77, exiting through the perforations 74a-77a into the uterine cavity. The tubes 74 and 75 are expandable for positioning adjacent the endometrium, with tubes 76 and 77 providing additional support and/or additional openings for flow of the therapeutic agent into the endometrium. The tubes can be made of a self-expanding material or a flexible material that automatically moves to the expanded position when exposed from the sheath. Alternatively, the tubes can have an internal wire positioned therein, similar to the internal wires disclosed herein, such as wires 14 or 24, which expand when exposed from the sheath to thereby expand the tubes to the position of FIG. 10A. The network of tubes shown is only one possible arrangement, and a greater or fewer number of tubes can be provided as well as a different arrangement of tubes other than that shown as long as the therapeutic agent is sufficiently dispersed throughout the uterine cavity. The tubes could be interconnected with each other, or alternatively, they could remain not connected to each other with each tube having an independent flow of the agent from the shaft. One example of an alternate arrangement of the tubes is shown in FIG. 10B wherein only two tubes 82, 84 are provided as sufficient to fill the cavity and dispense/disperse sufficient agent. In all other respects, device 80 is identical to device 70, e.g., has tube perforations 82a 84a, shaft 88, sheath 89, etc. so for brevity discussion of these components/features is not provided. FIG. 10C illustrates an alternate embodiment with a single straight (linear) perforated tube 85 and is an example of a non-expanding dispensing member. FIG. 10D illustrates another alternate embodiment with a hook shaped perforated tube 87.

The foregoing apparatus can include in some embodiments a feature that allows users to confirm that the dispensing member has opened and see how wide it has opened. This is shown in FIG. 12 wherein width indicator of apparatus 90 has markings 91 which indicate the width of the opening of the dispensing member which is in the form of balloon 92 to ensure the balloon has fully deployed within the uterine cavity. As the internal wire 94 which expands the balloon 92 is expanded as shown, it applies a force on the indicator wire 96, pulling portion 96a distally which pulls the marker 98 distally to indicate the extent of expansion of the balloon 92 by its position with respect to numeric makings 91. Other markings are also contemplated. This feature could be useful to ensure the dispensing is fully deployed as well as helpful in determining a needed volume of the chemical agent.

Any of the devices disclosed herein can include protective plugs to prevent or minimize the flow of the therapeutic agent into the fallopian tubes/and or into the cervix. An example of such plugs is shown in FIG. 11 wherein apparatus 100 has a plug 104 at distal end regions, e.g., distal corners, of the balloon 102 to block the therapeutic (treatment) agent, e.g., the chemical agent such as TCA, from flowing into the fallopian tubes F where it could damage the fallopian tubes. A plug 106 is positioned at a proximal region of the balloon 102, attached to the outer wall of the inner shaft 108 as shown, or alternatively, attached to a proximal portion of the balloon 102, to block the flow of the agent proximally into the cervix. Alternatively, a small balloon could be utilized in place of one or more of the plugs 104, 106. The proximal plug in alternate embodiments can include an annular balloon around the sheath 109 to seal the cavity from leaks of the agent or air through the cervix. In some embodiments, the plug can be slidable along the sheath or shaft or mounted to the sheath as in FIG. 2. If the cervix is sealed with such balloon or plug, and the fallopian tubes are closed or blocked and there is no uterus perforation, the entire cavity is sealed.

In preferred embodiments, the perforated dispensing member is configured and dimensioned so that when expanded its outer wall is close to but not necessarily in contact with the endometrium. However, it is also contemplated that the dispensing member can be configured and dimensioned so that when expanded it conforms to the contour of the uterus, thereby expanding to be in contact (abutment) with the endometrium. An example of such oversized perforated dispensing member for passage of the therapeutic agent is shown in FIG. 13 wherein the dispensing (dispersing) member 112 of apparatus 110 is in the form of a balloon. The dimensions of the balloon 112 are greater than that of the aforedescribed embodiments so as to more fully fill the uterine cavity. That is, when deployed, the dispensing member 112 will be compressed by the wall of the uterus and forced to comply/conform with the shape of the cavity. The balloon 112 could be reinforced with a structural wire 114 that is biased outward as in the wires discussed above. Such oversized dispensing member can be utilized with any of the embodiments disclosed herein. Note also the embodiments having perforated tubes could utilize tubes which expand further to come into contact (abutment) with the endometrium.

Figure 8A:
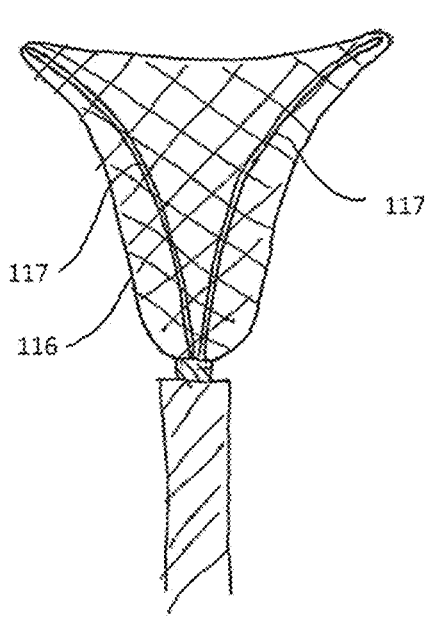
FIGS. 8A and 8B are cross-sectional views of alternate embodiments showing the configuration of the wires so that the sides of the balloon are spaced to increase thickness.
Figure 8B:
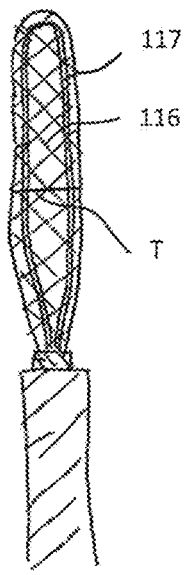
Figure 9:
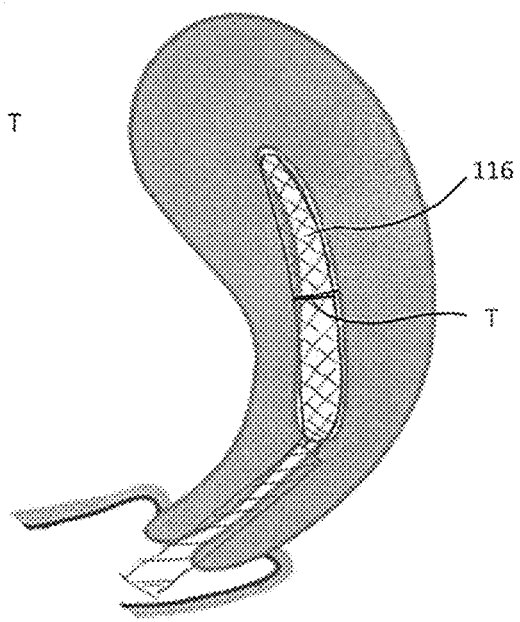
FIG. 9 is lateral cross-sectional view of the uterus showing the balloon of FIG. 8A inside the uterine cavity with a thickness to ensure contact with the wall of the uterine cavity.

FIGS. 8A, 8B and 9 show an alternate embodiment wherein the balloon is expanded in three dimensions. In the other embodiments disclosed herein, the balloons are essentially expanded in two dimensions as they are relatively flat. In this embodiment, dispensing member (balloon) 116 has looped shaped wires 117 to expand the balloon in three dimensions, providing an increased thickness T of the balloon 116 as shown in the lateral cross-section of the uterus with the balloon inside of the uterine cavity (FIG. 9). The structural wire 117 is configured such that the sides of the balloon 116 are spaced to assure the needed thickness. The thickness of the balloon 116 is such that it facilitates contact with the wall of the uterine cavity so the wall gets exposed to the therapeutic agent even if it is injected at a low pressure.

FIGS. 14A and 14B illustrate one embodiment of the actuator of the apparatus for exposing the dispensing/dispersing member for expansion. This is shown utilizing apparatus 10 of FIG. 1 by way of example, it being understood that the other apparatus disclosed herein, including the various aforedescribed balloons, wire structures, perforated tubes, etc., can use the same handle and actuator of FIGS. 14A and 14B to effect exposure of the dispensing member at the distal end of the shaft. Apparatus 10 has a handle 120 with a slidable actuator 122, e.g., a slidable button, movable within slot 124 of handle 120. The actuator 122 is operatively connected to the outer tube (sheath) 19 and is movable between a distal position wherein the sheath 19 is in the distal (extended) position and the balloon 11 and wire 14 are in the collapsed (reduced profile) position within the sheath 19 and a proximal (retracted) position wherein the sheath 19 is retracted to expose the balloon 11 and wire 14 for expansion to the expanded position within the uterine cavity. Alternatively, the sheath 19 could be stationary and attached to the handle, while the shaft 18 is operatively connected to the slidable actuator so that the shaft would be advanced by pushing the sliding button to the forward (distal) position to expose and expand the dispensing member. Other actuators are also contemplated.

The apparatus of FIGS. 14A and 14B also include a suction line 126 and a fluid input line 128 which includes a cavity integrity checking feature. This is discussed below in conjunction with FIGS. 16-18.

Turning now to the systems of the present invention which include the fluid and suction lines, FIG. 15 illustrates an embodiment with a separate syringe for the uterine cavity integrity check and for the therapeutic agent. Both syringes are connected to the shaft of the apparatus downstream of the handle. FIG. 16 illustrates an alternate system wherein a separate console is provided upstream of the handle with a switching mechanism for injection of the fluid for the cavity integrity check and for injection of the agent. The terms downstream and upstream as used herein refer to the direction of fluid flow into the cavity—fluid is injected and flows in a downstream direction.

Turning first to the system of FIG. 15, the system includes a syringe 130 containing the therapeutic agent and a syringe 140 for checking the pressure within the uterine cavity and is shown in conjunction with the apparatus 10 by way of example, although the syringes 130, 140 can be used in the same manner in conjunction with the other apparatus disclosed herein. More specifically, syringe 140 has a tube 142 connecting the barrel 144 to the channel, e.g. channel 18a of shaft 18, which forms the fluid line. The tube 142 is inserted through side port 17a of the apparatus 10 for fluid communication with the channel. A pressure gauge 143 is also provided on the syringe 140 for measuring pressure within the uterine cavity. When the plunger 145 is advanced, fluid such as a gas, e.g., $CO_2$, air, etc. or a liquid such as sterile water or saline, is advanced from barrel 144 into the line (tube) 142, into the channel 18a of shaft 18 and out through the distal opening of the channel 18a into the uterine cavity. Intrauterine pressure is monitored as the fluid (gas or liquid) is injected. Typically the fallopian tubes are closed, and it typically takes a pressure of 60-80 mm Hg to open them up. Since the intent is to avoid flow of the agent through the fallopian tubes, especially if a chemical ablative agent is used, in this embodiment, the cavity integrity is checked by inflating it to a pressure level that is lower than 60-80 mm Hg. This pressure level is sufficient to create a leak of fluid if the uterine cavity is perforated. Thus, after the pressure level is achieved, the injection is ceased and the pressure of the cavity is observed utilizing pressure gauge 143. If the pressure remains constant after termination of liquid or gas input, this will signify there is no leakage, thereby indicating that there are no perforations in the uterus and that the fallopian tubes are closed and that the uterine cavity is sealed for application of the therapeutic agent. If on the other hand the pressure drops after injection ceases, this will indicate that gas or liquid is escaping and the fallopian tubes are open and/or there are perforations in the uterus, thus informing the clinician that the uterine cavity is not sufficiently sealed and the therapeutic agent should not be applied. Note the syringe can be used to initially apply suction to the uterine cavity via retraction of the plunger 145 of syringe 140 to remove air bubbles prior to injection of the gas of liquid for checking the integrity of the uterine cavity. Additionally, after the cavity integrity check/test is completed, the gas or liquid can be suctioned/evacuated by reverse movement of the plunger 145 of the syringe 140. Note the above pressure levels are based on current testing, it being understood that other pressure levels are also within the scope of the invention.

The syringe 130 that can be similar to syringe 140 and could be equipped with a pressure gauge has an injection line 132 which is in fluid communication with the channel 18a of shaft 18 via attachment to side port 17b of outer tube 19. Movement of the plunger 134 forces the therapeutic agent, e.g. chemical ablative agent, out of barrel 136 and into injection line (tube or shaft) 132 for passage into channel 18a and into the balloon 11, where it exits through the balloon perforations 12 into the uterine cavity to ablate the endometrium. The syringe 130 is actuated after the syringe 140 confirms the uterine cavity is sealed to ensure that the chemical ablation substance or other agent being injected does not exit the uterine cavity and damage the fallopian tubes or other areas of the body. If the syringe 130 is equipped with the pressure gauge, the injection pressure is maintained at the level equal or below the pressure level at which the integrity of the uterine cavity was tested.

The slidable actuator 122 is operatively connected to outer tube (sheath) 19 so that movement of the actuator 122 retracts outer tube 19 so the balloon 11 and internal wire 14 attached to shaft 18 are exposed from outer sheath 19 so the balloon 11, via the radial force of the wire 14, expands to the expanded position shown in the same manner as described with respect to FIGS. 14A and 14B.

In use, the balloon (dispensing/dispersing) member 11 is expanded by proximal movement of the sheath 19 via actuator 122. After expansion of the balloon 11 and prior to injection of the chemical ablative agent (or other therapeutic agent), the syringe 140 is operated to inject gas (or liquid) though line 142 and through the channel 18a and out the distal opening of channel 18a into the uterine cavity to conduct the cavity integrity check. If the integrity of the uterine cavity is confirmed, i.e., there is no leakage into the fallopian tubes or other parts of the body from the uterus, the injected gas (or liquid) is evacuated by the syringe 140, then the syringe 130 is actuated to advance the agent though line 132 and through the perforations 12 in expanded balloon 11 to contact, e.g., chemically ablate the endometrium. As noted above, the other apparatus described above can be utilized with the system of FIG. 15 in the same manner as apparatus 10, i.e., dispensing member deployed by an actuator 122, cavity integrity checked by syringe 140, agent injected by syringe 130, etc. Thus, the other apparatus disclosed herein can include side ports for receipt of the syringes 130, 140 distal of the handle 120.

Figure 17:
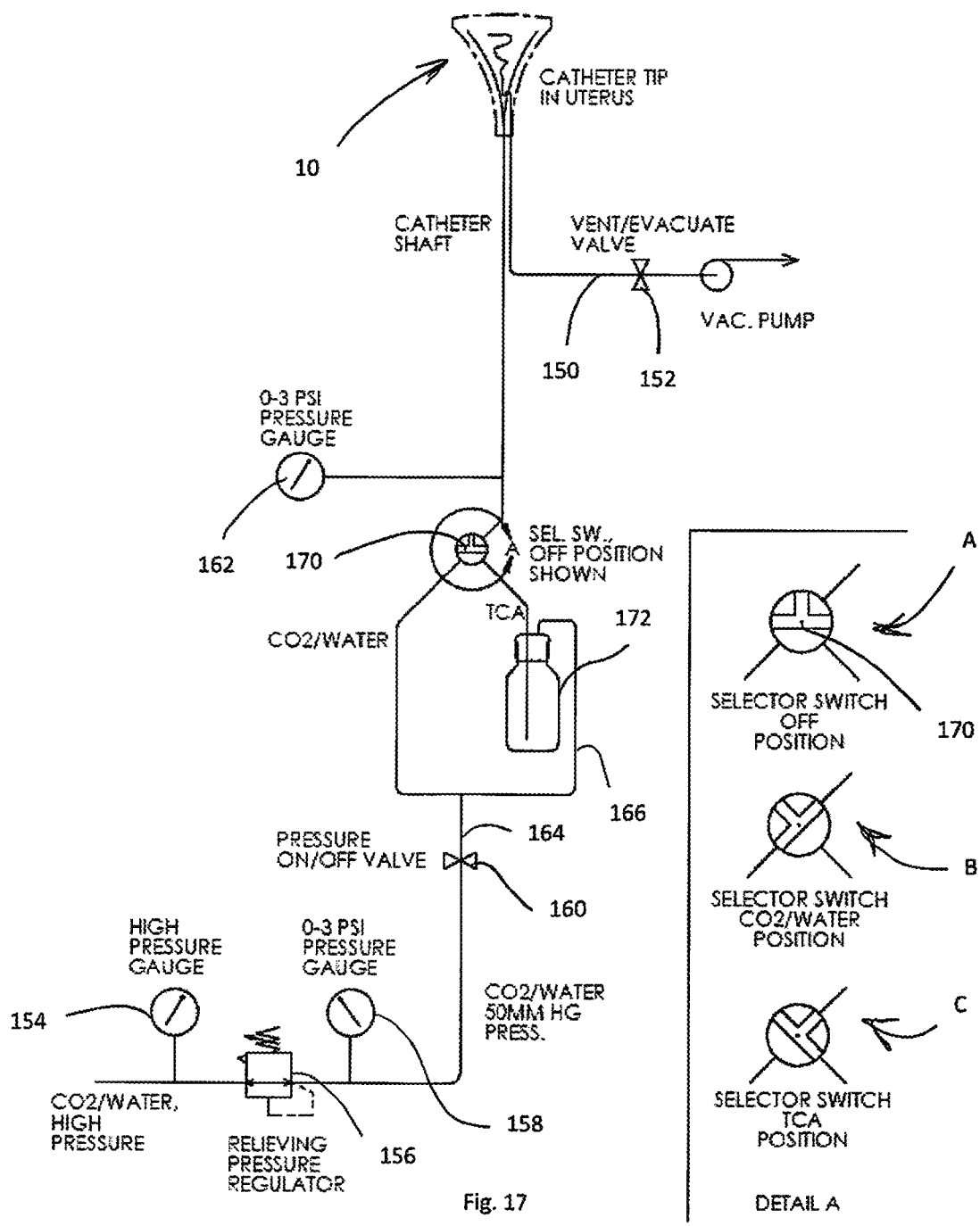
FIG. 17 is a schematic view of the system of FIG. 16.
Figure 18:
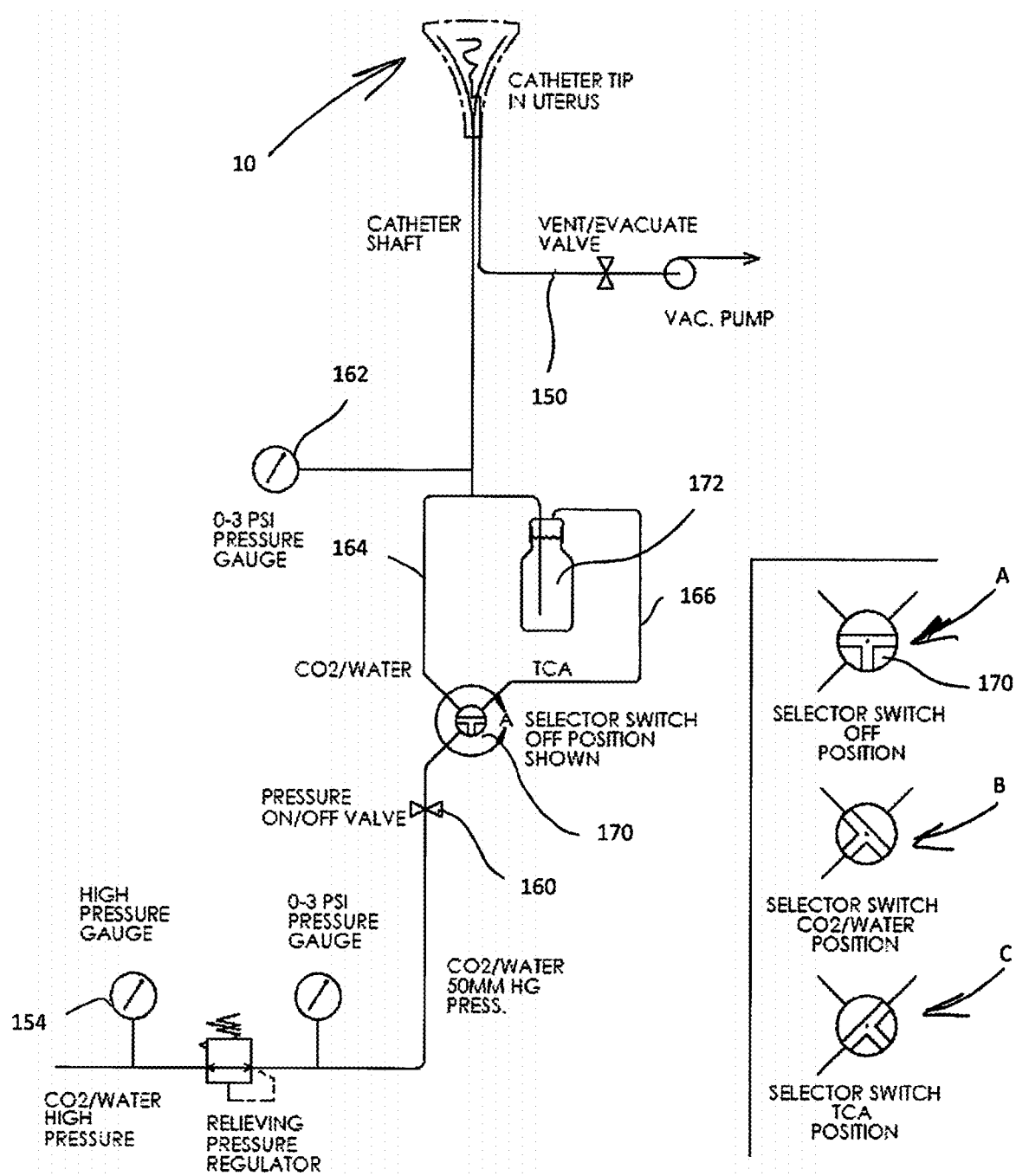
FIG. 18 is a schematic view similar to FIG. 17 except showing an alternate embodiment for placement of the switch.

FIGS. 16-18 illustrate alternative embodiments of the system of the present invention wherein suction and injection lines extend through the handle of the apparatus. These provide an alternative approach to a cavity integrity checking feature, utilizing a single pressurized fluid source combined with the manifold to conduct the cavity integrity check and injection of the therapeutic agent. The manifold is in the form of a control switch which allows the user to connect the fluid injection line to multiple lines inside of the delivery system. The lines are controlled by the manifold described in conjunction with the schematic diagrams of FIGS. 17 and 18. FIG. 18 illustrates a system wherein the manifold is reusable because it is not contaminated by the therapeutic agent, e.g., chemical agent; FIG. 17 illustrates an alternative system wherein the therapeutic agent, e.g., chemical agent, flows through the manifold and therefore is disposable (not reusable) since it is contaminated by the agent. Otherwise, these systems are the same. FIG. 16 is a perspective view of the system showing the console 180 which contains the selector switch 170 and supports the therapeutic agent within container 172, e.g. a jar or vial, which is connected via an injection line to the delivery channel for delivery into the uterine cavity. The console also includes a pressure gauge 174. The input line (input tube) 182 to the console 180 is for the high pressure gas or liquid into the manifold and the output line (outlet tube) 184 is for the pressurized gas or liquid or pressured agent from the manifold. Line (tube) 186 is for suction. The apparatus, e.g. apparatus 10, is connectable to the console 180 via tube 184. If sterile saline is used, the console can have a receptacle to receive a container, a jar, of sterile saline. Note that the apparatus and the console can be packaged together or packaged separately.

Turning first to the embodiment of FIG. 17, the catheter shaft and expanded dispensing member are shown schematically and can include any of the shafts and dispensing members discussed above. A suction line (tube) 150 (see also tube 186 of FIG. 16) communicates with the internal channel of the shaft and extends from an external vacuum pump. A vent/valve 152 turns the suction on and off. When the pump valve is in the open position, suction is applied to the uterine cavity for evacuation of the uterine cavity The suction line can be turned on at various stages of the procedure including one or more of the following: 1) initially before the pressurized fluid is injected for performing the cavity integrity check to remove air bubbles; 2) after the cavity integrity check to remove the liquid or gas from the uterine cavity that was used for the cavity check; and/or 3) after application of the therapeutic agent to the endometrium to remove agent from the uterine cavity.

With continued reference to the diagram of FIG. 17, a gas such as carbon dioxide $CO_2$ or liquid such as sterile water $H_2O$ high pressure system is connected to the apparatus (catheter) 10. The high pressure system can be a tank, a hospital unit, a cartridge, etc. or any other component that stores and injects the gas or liquid. A high pressure gauge 154 can optionally be provided to indicate the pressure within the storage device. The high pressure system also includes a pressure regulator 156 to reduce the pressure from the high pressure source. The regulator is adjustable to set the pressure to the desired amount, e.g., 0-3 psi (0-155 mm Hg). A pressure gauge 158 can be provided on the low pressure side to measure the pressure after reduced by the pressure regulator 156. After the pre-calculated amount of fluid is injected into the uterine cavity or the fluid is injected at the desired controlled pressure with the pressure monitored by pressure gauge 162 positioned upstream of the manifold, the pressure valve 160 is turned off and the pressure is monitored by the pressure gauge 162 (see also gauge 174 of FIG. 16). If there is a pressure drop, this indicates that there is a leakage from the uterine cavity. On the other hand, if the pressure remains constant, this confirms there is no leakage from the uterine cavity and the cavity is sufficiently sealed for application of the therapeutic agent. In addition or as an alternative, a flow meter can be provided to perform the cavity integrity check. That is, the meter can determine if flow ceases. If the flow in the uterine cavity of the gas or liquid ceases after a period of time because the cavity is full so it cannot accept more fluid, then it is confirmed there is no leakage. However, if flow continues, then it indicates there is a leakage of fluid from the uterus. Thus, as can be appreciated, instead of checking for pressure decay, fluid flow can be measured to check the integrity of the cavity.

The manifold is in the form of switch 170 which has three positions: 1) a neutral position (Position A) wherein the selector switch 170 is in the off position; 2) a second position (Position B) wherein the selector switch 170 is in a cavity integrity checking position; and 3) a third position (Position C) wherein the selector switch 170 is in a therapeutic agent (e.g. TCA) injection position. In Position A, the fluid line 164 from the pressure source is not in fluid communication with the tube connecting to the fluid channel within the shaft so there is no injection of pressurized fluid into the uterine cavity. In Position A, the fluid line is also not in fluid communication with the fluid line 166 for injection of the therapeutic agent so there is no injection of agent. In Position B, the fluid line 164 is fluidly connected to the tube connecting to the fluid channel so the pressurized fluid can be injected into the uterine cavity to perform the integrity check. In Position B, the fluid line is not in communication with the line 166 for injection of the therapeutic agent so there is no injection of the agent. In Position C, the fluid line 164 is in fluid communication with line 166 not line 164 for injection of pressurized fluid into the therapeutic agent storage device 172 to inject the agent under pressure into the dispensing member (preferably relatively low pressure but greater than if not pressurized) and through the perforations in the dispensing member into contact with the endometrium.

The system as noted above also includes a pressure gauge 162 (or 174), positioned distal/downstream of the manifold to measure the pressure within the uterine cavity. This ensures the pressure within the cavity does not exceed a maximum level that could cause outflow from the cavity or damage to the cavity. The pressure gauge measures the pressure for injection of the therapeutic agent. That is, the pressure level is preset (e.g. at 50 mm Hg or at 40 mm Hg) for the cavity integrity check at a level where there is no leakage (to provide a Go or No-Go test), it informs the user that the agent can be injected into the cavity at a pressure equal to or less than the measured fluid pressure (from the cavity check) without leakage or damage due to excess pressure. That is, the integrity cavity check also ensures the agent is applied at a safe pressure. Stated another way, the cavity checking feature applies the gas or liquid at a pressure where it is determined there is no leakage through perforations in the uterine wall or into the fallopian tubes. With knowledge of this pressure, the therapeutic agent can be applied at the same pressure (or a lower pressure) to ensure no leakage of the agent.

It is also contemplated that the manual manifold (switch) described herein could be replaced by an automated system that switches the connection from one line to another. Additionally, it is contemplated that the suction line can be designed to be controlled by the manifold or an automated system.

The system of FIG. 18 is identical to the system of FIG. 17 except for the placement of the manifold in the fluid line. That is, the switch 172 is upstream of the therapeutic agent so that the agent flows through the manifold. In all other respects, the features/components and functions of FIG. 17 are fully applicable to the system of FIG. 18 so for brevity are not repeated herein. The identical reference numerals of FIG. 17 are used for corresponding parts in FIG. 18.

In use of the systems of FIGS. 17 and 18 for performing for example chemical ablative endometrial ablation, the suction valve is first opened to apply a vacuum to the uterine cavity. Next, suction valve 150 is turned off and the dispensing member is expanded in the uterine cavity by relative movement of the shaft and outer tube, utilizing for example the slidable actuator. The switch 170 is moved from the neutral position (Position A) to the second position (the cavity check position—Position B) and the valve 160 is moved to the open position to enable the pressurized fluid to flow into the uterine cavity. The pressure gauge 162 monitors the pressure in the manner described above. Then the pressure valve 160 is turned off, and the suction valve 150 is moved to the on position to evacuate the fluid from the uterine cavity. After evacuation, the suction valve 150 is returned to the off position and the switch 170 is moved to the third position (agent injection position—Position C). The valve 160 is turned back on so pressurized fluid can flow into the storage container containing the therapeutic agent and the agent is injected under pressure through the dispensing member and into the uterine cavity for chemical ablation. After the ablation procedure, the valve 160 is turned off to cease the flow of the chemical agent, and the suction valve 150 is turned back on to suction the remaining chemical agent from the uterine cavity. The suction valve is then turned off. The dispensing member is returned to the collapsed position within the sheath by relative movement of the sheath and shaft and the apparatus is removed from the uterine cavity. Note the foregoing provides one example of the method of use.

It is contemplated to add an element on the fluid input line that is not compatible with the chemical agent (e.g., TCA) so that it would degrade during the procedure to prevent reuse. For example, a cover or collar made of plastic can be positioned over a portion of the tube, for example, inside the handle, which plugs a side hole in the tube. As the plastic degrades, the side opening would become unplugged so that fluid would exit through the side opening. This would provide an indicator and prevent reuse of the system.

As noted above the apparatus described herein can provide a chemical global endometrium ablation device for the treatment of Abnormal Uterine Bleeding (AUB). The apparatus is a small profile non-invasive device that combines simplicity, cost effectiveness and ease-of-use of the IUD devices with the clinical efficacy of the GEA devices making available for use in the office environment by OBGYN practitioners to treat AUB without learning any new skills. In some embodiments, the catheter can have an outer diameter of less than or equal to 3 mm, and is flexible and atraumatic and can eliminate the need for cervical dilations.

As noted above, the apparatus and systems disclosed herein are described by way of example for use for chemical ablation of the endometrium for endometrium ablation. However, the apparatus and systems disclosed herein can be used to apply other therapeutic agents to the uterine cavity as well as can also be used for injecting chemical ablative or other therapeutic agents to other regions or cavities of the body.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. An apparatus for delivering a therapeutic agent to a uterine cavity of a patient comprising
    a) an elongated member having a fluid channel for passage of the therapeutic agent into the uterine cavity of the patient, the fluid channel having an opening;
    b) a dispensing member extending distally of the elongated member and in communication with the fluid channel, the dispensing member having a first condition for delivery having a first transverse dimension and a second condition for placement within the uterine cavity having a second transverse dimension greater than the first transverse dimension, the dispensing member having at least one perforation to provide at least one exit opening for passage of the therapeutic agent into the uterine cavity into contact with an endometrium, the therapeutic agent injectable through the at least one perforation at a controlled pressure;

c) wherein the therapeutic agent is a chemical ablative agent for endometrial ablation;

d) wherein a fluid is injected into the uterine cavity prior to injection of the ablative agent, and the ablative agent is injected at a pressure less than or equal to the pressure of injection of the fluid, the injection of the fluid assesses the presence or absence of leakage in the uterine cavity; and e) a switch having a first position for enabling flow of the fluid through the fluid channel to assess the presence or absence of leakage and a second position for enabling injection of the ablative agent through the fluid channel.

2. The apparatus of claim 1, wherein the fluid injected to assess the presence or absence of leakage is subsequently injected to inject the ablative agent through the fluid channel at an increased pressure.

3. The apparatus of claim 1, wherein the dispensing member comprises an expandable member and at least one wire positioned within the member, the wire expanding the member prior to injection of the therapeutic agent into the member.

4. The apparatus of claim 1, wherein the dispensing member comprises a plurality of perforated tubes.

5. The apparatus of claim 1, further comprising a suction line to evacuate the uterine cavity, the suction line communicating with the fluid channel.

6. The apparatus of claim 1, further comprising a pressure gauge.

7. An apparatus for delivering a therapeutic agent to the uterine cavity comprising:

a) an elongated member having a fluid channel for passage of the therapeutic agent into a uterine cavity of a patient, the fluid channel having an opening;

b) a dispensing member extending distally of the elongated member, the dispensing member having at least one perforation to provide at least one exit opening for passage of the therapeutic agent into the uterine cavity into contact with an endometrium;

c) an infusion line in communication with the fluid channel for passage of a fluid into the uterine cavity to assess leakage to determine integrity of the uterine cavity prior to passage of the therapeutic agent into the uterine cavity, wherein the therapeutic agent is injected at a pressure equal to or less than the pressure of the fluid during determining the integrity of the cavity; and d) a switch movable from a first to a second position, wherein the first position enables injection of the fluid through the fluid channel into the uterine cavity to determine the integrity of the uterine cavity and the second position enables injection of the fluid into the storage unit to inject the therapeutic agent at the increased pressure.

8. The apparatus of claim 7, wherein the dispensing member comprises an expandable member and at least one wire positioned within the expandable member, the wire expanding the expandable member prior to injection of the therapeutic agent into the member.

9. The apparatus of claim 7, wherein the dispensing member comprises a plurality of perforated tubes.

10. The apparatus of claim 7, wherein the therapeutic agent comprises a chemical ablative agent.

11. The apparatus of claim 7, wherein the therapeutic agent is injected at a minimum pressure to ensure maximum exposure and below a maximum pressure to prevent leakage.

12. The apparatus of claim 7, further comprising a plug positioned proximal of the dispensing member to prevent leakage of the ablative agent into a patient's cervix.

13. The apparatus of claim 7, wherein the fluid injected into the uterine cavity to determine integrity of the uterine cavity is subsequently injected into a storage unit containing the ablative agent to inject the ablative agent at an increased pressure through the fluid channel, the pressure being less than a pressure that would cause leakage.

* * * * *